(12) United States Patent
Uzzo

(10) Patent No.: US 12,377,235 B2
(45) Date of Patent: Aug. 5, 2025

(54) MULTIPURPOSE DEVICE

(71) Applicant: Institute For Cancer Research, Philadelphia, PA (US)

(72) Inventor: Robert G. Uzzo, Philadelphia, PA (US)

(73) Assignee: INSTITUTE FOR CANCER RESEARCH, Philadelphia, PA (US)

(*) Notice: Subject to any disclaimer, the term of this patent is extended or adjusted under 35 U.S.C. 154(b) by 1192 days.

(21) Appl. No.: 16/965,706

(22) PCT Filed: Jan. 28, 2019

(86) PCT No.: PCT/US2019/015340
§ 371 (c)(1),
(2) Date: Jul. 29, 2020

(87) PCT Pub. No.: WO2019/152296
PCT Pub. Date: Aug. 8, 2019

(65) Prior Publication Data
US 2021/0038842 A1    Feb. 11, 2021

Related U.S. Application Data

(60) Provisional application No. 62/730,600, filed on Sep. 13, 2018, provisional application No. 62/623,707, filed on Jan. 30, 2018.

(51) Int. Cl.
*A61M 16/04*        (2006.01)
*A61H 9/00*         (2006.01)
(Continued)

(52) U.S. Cl.
CPC .......... *A61M 16/049* (2014.02); *A61H 9/005* (2013.01); *A61M 16/0057* (2013.01);
(Continued)

(58) Field of Classification Search
CPC .... A61M 16/00–0003; A61M 16/0051; A61M 16/0057–0084; A61M 16/20–209; A61M 2016/0015–0042; A61B 5/085–087; A61B 5/0875; A61B 5/09; A61H 9/00–0007; A61H 9/0078; A61H 9/0092; A61H 2201/0103
See application file for complete search history.

(56) References Cited

U.S. PATENT DOCUMENTS

| 471,389 A | * | 3/1892 | Lacey | A61B 5/0871 73/744 |
| 3,633,421 A | * | 1/1972 | Phillips | G01F 1/22 137/558 |

(Continued)

OTHER PUBLICATIONS

International Search Report and Written Opinion for PCT Application PCT/US2019/015340.

*Primary Examiner* — Rachel T Sippel
(74) *Attorney, Agent, or Firm* — Ballard Spahr LLP

(57) ABSTRACT

A multipurpose device for preventing or treating deep vein thrombosis, extremity edema, and breathing conditions is provided herein. The multipurpose device includes a respiratory device, such as a flutter valve or a spirometer, having a mouthpiece or nasal breathing piece, a pump connected to the respiratory device by first tubing, a release valve connected to the pump by second tubing, and one or more third tubing(s) connected to the release valve.

17 Claims, 2 Drawing Sheets

(51) Int. Cl.
*A61M 16/00* (2006.01)
*A61M 16/06* (2006.01)
*A61M 16/20* (2006.01)

(52) U.S. Cl.
CPC .... *A61M 16/0486* (2014.02); *A61M 16/0666* (2013.01); *A61M 16/209* (2014.02); *A61M 2016/003* (2013.01)

(56) References Cited

U.S. PATENT DOCUMENTS

| | | | | |
|---|---|---|---|---|
| 3,985,131 | A * | 10/1976 | Buck | A61M 16/024 |
| | | | | 128/205.24 |
| 6,010,470 | A * | 1/2000 | Albery | A61H 9/0092 |
| | | | | 601/149 |
| 8,001,966 | B1 * | 8/2011 | Goldstein | A61M 16/209 |
| | | | | 128/204.22 |
| 2004/0249300 | A1 | 12/2004 | Miller | |
| 2005/0126578 | A1 * | 6/2005 | Garrison | A61H 9/0078 |
| | | | | 128/874 |
| 2006/0231100 | A1 * | 10/2006 | Walker | A61M 16/08 |
| | | | | 128/205.25 |
| 2007/0068518 | A1 | 3/2007 | Urias et al. | |
| 2011/0030141 | A1 * | 2/2011 | Soderberg | A61M 5/172 |
| | | | | 5/600 |
| 2015/0224012 | A1 * | 8/2015 | Wright | A61H 9/0078 |
| | | | | 601/150 |
| 2015/0265874 | A1 | 9/2015 | Rettig | |
| 2018/0014995 | A1 * | 1/2018 | Gensch | A61H 9/0085 |
| 2020/0345962 | A1 * | 11/2020 | Hansmann | A61M 16/127 |
| 2021/0220217 | A1 * | 7/2021 | Zony | A61B 6/0414 |

* cited by examiner

MULTIPURPOSE DEVICE

FIELD

The present disclosure relates generally to multipurpose devices that can be used to treat and/or prevent vascular events and various respiratory conditions.

BACKGROUND

Deep vein thrombosis is a condition that occurs when a blot clot forms in one or more of the deep veins of the body. Most typically, the clot forms in the deep veins of the lower legs. Deep veins are those that are located well within the interior of the limbs. Deep vein thrombosis is often caused by immobility of the limbs, for example, by prolonged sitting, or by surgery or trauma. Multiple risk factors for deep vein thrombosis include pregnancy, obesity, immobility, and genetic predispositions. The formation of the clot can cause pain and swelling of the affected limb. More seriously, the clot can dislodge and cause an embolism, such as a pulmonary embolism (blood clot lodged in the lungs). If untreated, a deep vein thrombosis can lead to damage of the limbs, or even death.

For hospitalized patients, electrical pneumatic devices are often employed with various compression stockings to help mitigate against the formation of deep vein thrombosis. These devices are attached to the limbs, and are inflated and deflated to pressurize the tissue and facilitate blood flow. These devices are not portable and require electrical current. Hospitalized patients also may receive pharmacological prophylaxis to prevent DVTs, but not all patients can receive them due to other conditions and predispositions. Hospitals have a current need to improve outpatient DVT prophylaxis by offering patients some alternative to electric-based pneumatic stockings when they transition out of the hospital. In particular, there is a need for something that will improve compliance, decrease the risk of recurring DVTs, and decrease readmissions and hospital liability.

The present disclosure fulfills this need by allowing the patients transitioning out of the hospital to their home to continue to use the pneumatic compression stockings that the patient was already using in the hospitals, but without the need for an electrical pump, which is expensive, not portable and impractical The multipurpose device of the present disclosure combines the features of a pneumatic pump that provides some level of physical activity, incorporates spirometry, and inflates the compression stockings they already used in the hospital.

SUMMARY

The present disclosure provides multipurpose devices comprising: a respiratory device; a pump connected to the respiratory device by first tubing; a release valve connected to the pump by second tubing; and one or more third tubing(s) connected to the release valve.

In some embodiments, the respiratory device is a spirometer. In some embodiments, the spirometer is an incentive spirometer, a peak flow spirometer, a windmill-type spirometer, a tilt-compensated spirometer, or fully electronic spirometer. In some embodiments, the spirometer is an incentive spirometer. In some embodiments, the spirometer is a peak flow spirometer. In some embodiments, the spirometer is a windmill-type spirometer. In some embodiments, the spirometer is a tilt-compensated spirometer. In some embodiments, the spirometer a fully electronic spirometer. In some embodiments, the respiratory device is a flutter valve.

In some embodiments, the respiratory device, such as the spirometer or flutter valve, comprises an air import, such as a nasal breathing piece or a mouthpiece. In some embodiments, the mouthpiece is a disposable mouthpiece, permanent mouthpiece, or a one-way valve mouthpiece. In some embodiments, the mouthpiece is a disposable mouthpiece. In some embodiments, the mouthpiece is a permanent mouthpiece. In some embodiments, the mouthpiece is a one-way valve mouthpiece.

In some embodiments, the respiratory device, such as the spirometer or flutter valve, comprises a receptor for an insert adjacent to the mouthpiece or nasal breathing piece. In some embodiments, the insert is a scented disc or a medicated disc. In some embodiments, the medicated disc is impregnated with an anti-anxiolytic or a bronchodilator. In some embodiments, the bronchodilator is albuterol.

In some embodiments, the respiratory device, such as the spirometer or flutter valve, comprises a whistle indicator. In some embodiments, the respiratory device, such as the spirometer or flutter valve, comprises graduated color or markings and an indicator ball or plunger.

In some embodiments, the respiratory device, such as the spirometer or flutter valve, comprises a variable sense valve or e-monitoring chip.

In some embodiments, any one or more of the first tubing, second tubing, and third tubing(s) is/are variable length. In some embodiments, the first tubing is expandable.

In some embodiments, the pump is a billow-type pump, an accordion-type pump, or a manual pneumatic pump. In some embodiments, the pump is a billow-type pump. In some embodiments, the pump is an accordion-type pump. In some embodiments, the pump is a manual pneumatic pump. In some embodiments, the pump is capable of being actuated by hand, foot, or thigh. In some embodiments, the pump, such as a billow, can be actuated manually or via an inflow of air by a motor, such as a mattress air pump type motor. In some embodiments, the pump further comprises one or more straps or fasteners.

In some embodiments, the one or more third tubing(s) comprises graduated color or markings and an indicator ball or plunger.

In some embodiments, the one or more third tubing(s) comprises a connector at the terminal end(s). In some embodiments, the device further comprises one or more compression stockings connected to the one or more third tubing(s) by the connector at the terminal end(s).

In some embodiments, the first tubing connecting the pump to the respiratory device, such as the spirometer or flutter valve, comprises a connector that is capable of disconnecting the first tubing from the pump.

In some embodiments, the release valve comprises a variable sense valve or e-monitoring chip.

The present disclosure also provides methods of using any of the multipurpose devices described herein, comprising: inserting the mouthpiece or nasal breathing piece of the respiratory device into the mouth or nose of a user; and inhaling and/or exhaling by the user via the respiratory device, such as the spirometer or the flutter valve. In some embodiments, when the device further comprises one or more compression stockings connected to the one or more third tubing(s) by the connector at the terminal end(s), the method further comprises activating the pump to load the one or more compression stockings with air. In some embodiments, the user is being treated to treat or prevent atelectasis. In some embodiments, the user has asthma or chronic obstructive pulmonary disease and is undergoing breathing exercises. In some embodiments, the user is undergoing relaxation breathing therapy or diversion therapy. In some embodiments, the user is being treated to prevent deep vein thrombosis.

BRIEF DESCRIPTION OF THE DRAWINGS

The present disclosure can be understood from the following detailed description when read in connection with the accompanying drawings. It is emphasized that, according to common practice, the various features of the drawings are not to scale. On the contrary, the dimensions of the various features are arbitrarily expanded or reduced for clarity. Included in the drawings are the following FIGURES.

DESCRIPTION OF EMBODIMENTS

Figure 1:
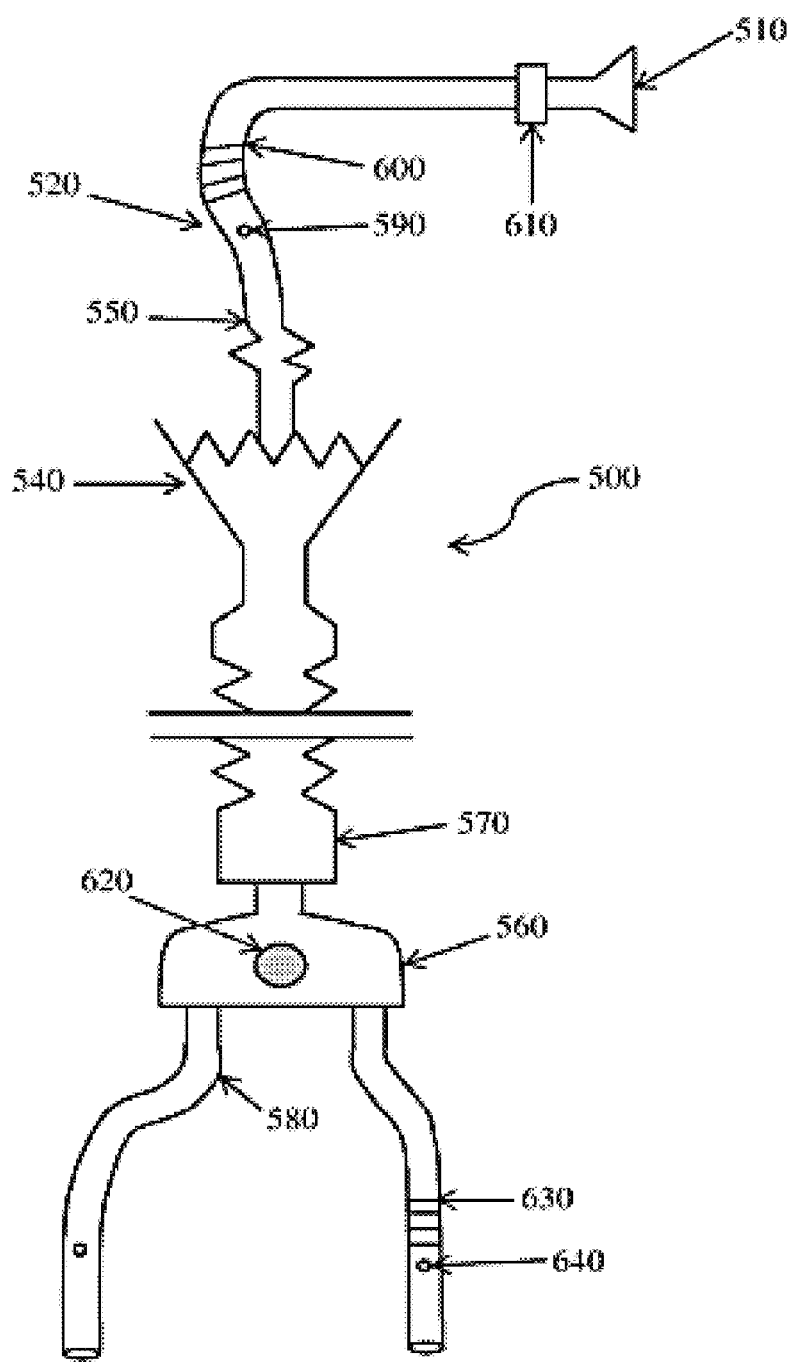
FIG. 1 shows a representative multipurpose device.

Various terms relating to aspects of the present disclosure are used throughout the specification and claims. Such terms are to be given their ordinary meaning in the art, unless otherwise indicated. Other specifically defined terms are to be construed in a manner consistent with the definition provided herein.

Various publications, including patents, published applications, technical articles and scholarly articles are cited throughout the specification. Each of these cited publications is incorporated herein by reference in its entirety and for all purposes.

As used herein, the singular forms "a," "an," and "the" include plural referents unless expressly stated otherwise.

The present disclosure provides multipurpose devices 500 comprising: a respiratory device 520; a pump 540 connected to the respiratory device 520 by first tubing 550; a release valve 560 connected to the pump 540 by second tubing 570; and one or more third tubing(s) 580 connected to the release valve 560.

In some embodiments, the respiratory device 520 is a breathing device to encourage pulmonary inspiration and/or expiratory therapy. In some embodiments, the respiratory device 520 is a spirometer. In some embodiments, the spirometer is an incentive spirometer, a peak flow spirometer, a windmill-type spirometer, a tilt-compensated spirometer, or a fully electronic spirometer. In some embodiments, the spirometer is an incentive spirometer. In some embodiments, the spirometer is a peak flow spirometer. In some embodiments, the spirometer is a windmill-type spirometer. In some embodiments, the spirometer is a tilt-compensated spirometer. In some embodiments, the spirometer is a fully electronic spirometer. The spirometer can be any of the commercially available spirometers.

In some embodiments, the respiratory device 520 is a flutter valve. The flutter valve can be any of the commercially available flutter valves.

In some embodiments, the respiratory device 520, such as the flutter valve or the spirometer, comprises an air import 510, such as a nasal breathing piece or a mouthpiece. In some embodiments, the air import 510 is a nasal breathing piece. In some embodiments, the air import 510 is a mouthpiece. In some embodiments, the mouthpiece is a disposable mouthpiece, a permanent mouthpiece, a mask mouthpiece, a nasal breathing piece, or a one-way valve mouthpiece. In some embodiments, the mouthpiece is a disposable mouthpiece. In some embodiments, the mouthpiece is a permanent mouthpiece. In some embodiments, the mouthpiece is a mask mouthpiece. In some embodiments, the mouthpiece is a one-way valve mouthpiece. The air import 510 can be any of the commercially available air imports.

In some embodiments, the respiratory device 520, such as the flutter valve or the spirometer, comprises graduated color or markings 600 and an indicator ball or plunger 590. Upon inhaling or exhaling, the indicator ball or plunger 590 can travel within the respiratory device 520 and the length traveled and force can be determined by examining the graduated color or markings 600 on the respiratory device 520. The distance the indicator ball or plunger 590 moves can be an indication of the intensity of the inhale or exhale. In some embodiments, the respiratory device 520, such as the flutter valve or the spirometer, comprises a whistle indicator (not shown). The whistle indicator is configured to produce a whistle noise upon inhaling or exhaling. The loudness of the whistle can be an indication of the intensity of the inhale or exhale.

In some embodiments, the respiratory device 520, such as the flutter valve or the spirometer, comprises a receptor 610 for an insert adjacent to the air import 510. The receptor 610 serves as a chamber for containing the insert. In some embodiments, the receptor 610 can be an aerosol receptor, a mist or vapor receptor, or a plunger. In some embodiments, the air can be warmed. In some embodiments, the receptor 610 can be provided with positive pressure ventilation, such as integration with an airbag or manual or pneumatic method of increasing the force of inspiration into the airway. In some embodiments, the insert is a scented disc or a medicated disc.

In some embodiments, the scented disc includes, but is not limited to, mint, lemon, lavender, jasmine, rosemary, cinnamon, peppermint, and other food flavoring such as grape, cherry, lemon, lime, etc.

In some embodiments, the medicated disc is impregnated with an anxiolytic, a bronchodilator, a sedative, or an analgesic.

In some embodiments, the bronchodilator is a short-acting bronchodilator or a long-acting bronchodilator. In some embodiments, short-acting bronchodilators include, but are not limited to, Proventil® or Ventolin® (salbutamol/albuterol), Xopenex® (levosalbutamol/levalbuterol), Maxair® (pirbuterol), Primatene Mist® (epinephrine), Asthmanefrin®, Primatene Mist® replacement (racemic epinephrine), Bronkaid® (ephedrine), or terbutaline. In some embodiments, the long-acting bronchodilator is Serevent® (salmeterol), Spiropent® (clenbuterol), formoterol, bambuterol, and indacaterol. In some embodiments, the bronchodilator is albuterol.

In some embodiments, the anxiolytic is a barbiturate, a benzodiazepine, a carbamate, an opioid, an antidepressant, or a sympatholytic. In some embodiments, antidepressants include, but are not limited to, selective serotonin reuptake inhibitors, serotonin-norepinephrine reuptake inhibitors, tricyclic antidepressants, tetracyclic antidepressants, or monoamine oxidase inhibitors. In some embodiments, barbiturates include, but are not limited to, allobarbital, amobarbital, aprobarbital, alphenal, barbital, brallobarbital, pentobarbital, phenobarbital, secobarbital, and thiopental. In some embodiments, benzodiazepines include, but are not limited to, Xanax® (alprazolam), Lectopam® or Lexotan® (bromazepam), Librium (chlordiazepoxide), Klonopin® or Rivotril® (clonazepam), Tranxene® (clorazepate), Valium® (diazepam), Dalmane® (flurazepam), Ativan® (lorazepam), Serax® or Serapax® (oxazepam), Restoril® (temazepam), and Halcion® (triazolam). In some embodiments, carbamates include, but are not limited to, meprobamate (Miltown®, Equanil®), tybamate, and lorbamate. In some embodiments, opioids include, but are not limited to, codeine, morphine, thebaine, oripavine, buprenorphine, etorphine, hydrocodone, hydromorphone, oxycodone, oxymorphone, diacetylmorphine, nicomorphine (morphine dinicotinate), dipropanoylmorphine (morphine dipropionate), diacetyldihydromorphine, acetylpropionylmorphine, desomorphine, methyldesorphine, dibenzoylmorphine, dihydrocodeine, ethylmorphine, heterocodeine, fentanyl, alphamethylfentanyl, alfentanil, sufentanil, remifentanil, carfentyl, sufentanil, ohmefentanyl, Meperidine® (pethidine), ketobemidone, MPPP, allylprodine, prodine, PEPAP, promedol, propoxyphene, dextropropoxyphene, dextromoramide, bezitramide, piritramide, methadone, dipipanone, levomethadyl acetate (LAAM), difenoxin, diphenoxylate, loperamide, lefetamine, menthol, meptazinol, mitragynine, tilidine, tramadol, tapentadol, eluxadoline, AP-237, and 7-hydroxymitragynine. Selective serotonin reuptake inhibitors include, but are not limited to, Celexa® (citalopram), Lexapro® (escitalopram), Prozac® (fluoxetine), Luvox® (fluvoxamine), Paxil® (paroxetine), and Zoloft® (sertraline). Serotonin-norepinephrine reuptake inhibitors include, but are not limited to, venlafaxine and duloxetine. Tricyclic antidepressants include, but are not limited to, imipramine, amitriptyline, nortriptyline, and desipramine. Tetracyclic antidepressants include, but are not limited to, mirtazapine. Monoamine oxidase inhibitors include, but are not limited to, phenelzine, isocarboxazid, tranylcypromine, and moclobemide. Sympatholytics include, but are not limited to alpha-adrenergic agonists such as clonidine and guanfacine. Additional anxiolytics include, but are not limited to, mebicar, fabomotizole, selank, bromantane, emoxypine, azapirones (such as Buspar® (buspirone) and Sediel® (tandospirone)), pregabalin, menthyl isovalerate, and propofol.

In some embodiments, the sedative is a barbiturate such as, for example, benzylbutylbarbiturate, butalbital, amobarbital, pentobarbital, secobarbital, sodium thiopental, and phenobarbital. In some embodiments, the sedative is a benzodiazepine such as, for example, clonazepam, diazepam, estazolam, flunitrazepam, lorazepam, midazolam, nitrazepam, oxazepam, triazolam, temazepam, chlordiazepoxide, alprazolam, clobazam, clorazepate, and etizolam. In some embodiments, the sedative is a nonbenzodiazepine hypnotic such as, for example, eszopiclone, zaleplon, zolpidem, and zopiclone. In some embodiments, the sedative is an orexin antagonist such as, for example, suvorexant. In some embodiments, the sedative is a first generation antihistamine such as, for example, diphenhydramine, dimenhydrinate, doxylamine, promethazine, hydroxyzine, brompheniramine, and chlorpheniramine. In some embodiments, the sedative is a general anesthetic such as, for example, nitrous oxide, sevoflurane, halothane, xenon, enflurane, chloroform, isoflurane, methoxyflurane, desflurane, ethyl chloride, cyclopropane, chloral hydrate, ketamine, esketamine, etomidate, propofol, and chlorobutanol. In some embodiments, the sedative is a herbal sedative such as, for example, *Duboisia hopwoodii*, chamomile, *Prostanthera striatiflora*, catnip, Kava (*Piper methysticum*), valerian, *cannabis, Passiflora* spp. (*Passiflora incarnata*), *Physochlaina* (*P. infundibularis*), and validol. In some embodiments, the sedative is methaqualone or analogues thereof such as, for example, afloqualone, cloroqualone, diproqualone, etaqualone, methaqualone, methylmethaqualone, mebroqualone, mecloqualone, and nitromethaqualone.

In some embodiments, the sedative is a skeletal muscle relaxant such as, for example, baclofen, meprobamate, carisoprodol, cyclobenzaprine, metaxalone, methocarbamol, tizanidine, chlorzoxazone, orphenadrine, gabapentin, and pregabalin. In some embodiments, the sedative is an opioid such as, for example, tramadol, tapentadol, morphine, hydromorphone, oxymorphone, oxycodone, hydrocodone, methadone, propoxyphene, meperidine, fentanyl, codeine, carfentanil, remifentanil, alfentanil, sufentanil, and opium. In some embodiments, the sedative is an antidepressant such as, for example, amitriptyline, trazodone, mirtazapine, doxepin, desipramine, imipramine, clomipramine, amoxapine, trimipramine, nortriptyline, and nefazodone. In some embodiments, the sedative is an antipsychotic such as, olanzapine, clozapine, thiothixene, haloperidol, fluphenazine, prochlorperazine, trifluoperazine, loxapine, quetiapine, and asenapine. In some embodiments, the sedative is another 2-methyl-2-butanol (2M2B) such as, for example, ethanol, glutethimide, GHB, and dextromethorphan.

In some embodiments, the analgesic is a non-narcotic analgesic, such as, for example, Tylenol® (acetaminophen). In some embodiments, the analgesic is a non-steroidal anti-inflammatory drug (NSAID), such as, for example, Prolensa® or Bromday® (bromfenac), Cataflam®, Voltaren® or Zipsor® (diclofenac), Dolobid® (diflunisal), Lodine® or Lodine® XL (etodolac), Nalfon® (fenoprofen), Ansaid® (flurbiprofen), Advil®, Cramp End®, Dolgesic®, Excedrin® IB, Genpril®, Haltran®, Ibren®, Ibu®, Ibuprin®, Ibuprohm®, Ibu-Tab®, Medipren®, Midol® IB, Motrin®, Nuprin®, Pamprin®-IB, Q-Profen®, Rufen®, or Trendar® (ibuprofen), Indocin®, Indocin® SR, or Tivorbex® (indomethacin), Actron®, Orudis® or Oruvail® (ketoprofen), Toradol® or Sprix® (ketorolac), Meclomen® (meclofenamate), Ponstel® (mefenamic acid), Mobic® or Vivlodex® (meloxicam), Relafen® (nabumetone), Aleve®, Anaprox®, Anaprox® DS, EC-Naprosyn®, Naprelan®, or Naprosyn® (naproxen), Nevanac® (nepafenac), Daypro® (oxaprozin), Cotylbutazone® (phenylbutazone), Feldene® (piroxicam), Clinoril® (sulindac), and Tolectin® or Tolectin® DS (tolmetin). In some embodiments, the analgesic is a COX-2 inhibitor, such as, for example, Celebrex® (celecoxib). In some embodiments, the analgesic is a narcotic pain medication, such as, for example, Buprenex® (buprenorphine), Stadol® (butorphanol), Codeine, Hydrocodone, Dilaudid®, Dilaudid-5®, Dilaudid®-HP, Hydrostat® IR, or Exalgo® ER (hydromorphone), Levo-Dromoran® (levorphanol), Demerol® (meperidine), Dolophine® or Methadose® (methadone), Astramorph® PF, AVINZA®, Duramorph®, Kadian®, M S Contin®, MSIR®, Oramorph® SR, Rescudose®, or Roxanol® (morphine), Nubain® (nalbuphine), OxyContin®, Roxicodone®, or Oxecta® (oxycodone), Numorphan® (oxymorphone), Talwin® (pentazocine), Cotanal-65® or Darvon® (propoxyphene), and Nucynta® (tapentadol). In some embodiments, the analgesic is a central analgesic, such as, for example, Ultram® (tramadol) and Ultracet® (tramadol and acetaminophen). In some embodiments, the analgesic is a combination, such as, for example, Femcet®, Fioricet®, Esgic®, or Esgic-Plus® (butalbital, acetaminophen, and caffeine), Fiorinal® (butalbital, aspirin, and caffeine), Fioricet® with codeine (butalbital, acetaminophen, caffeine, and codeine), Hydrostal® IR or Vicoprofen® (hydrocodone and ibuprofen), Embeda® (morphine and naltrexone), Troxyca® ER (oxycodone and naltrexone), Talwin® NX (pentazocine and naloxone), Capital® with Codeine, Margesic® #3, Phenaphen® with Codeine, or Tylenol® with Codeine (acetaminophen and codeine), DHCplus® (dihydrocodeine, acetaminophen, and caffeine), Allay®, Anexsia®, Anexsia® 5/500, Anexsia® 7.5/650, Dolacet®, Dolagesic®, Duocet®, Hycomed®, Hycrocet®, Hydrogesic®, HY-PHEN®, Lorcet® 10/650, Lorcet®-HD, Lortab®, Panacet® 5/500, Panlor®, Stagesic®, T-Gesic®, Ugesic®, Vicodin®, or Zydone® (hydrocodone and acetaminophen), Endocet®, Percocet®, Roxicet®, Roxilox®, Tylox®, or Xartemis® XR (oxycodone and acetaminophen), Talacen® (pentazocine and acetaminophen), Darvocet-N® 50, Darvocet-N® 100, E-Lor®, or Propacet® 100 (propoxyphene and acetaminophen), Synalgos®-DC (aspirin, caffeine, and dihydrocodeine), Empirin® with Codeine (aspirin and codeine), Damason-P®, Lortab® ASA, or Panasal® 5/500 (hydrocodone and aspirin), Endodan®, Percodan®, Percodan®-Demi, or Roxiprin® (oxycodone and aspirin), Talwin Compound (pentazocine and aspirin), Darvon Compound-65, PC-Cap®, or Propoxyphene Compound-65 (propoxyphene, aspirin, and caffeine).

In some embodiments, the respiratory device 520 comprises a variable sense valve or e-monitoring chip (not shown). Such a valve or chip can be configured to record breathing information (e.g., breathing rate, intensity of inhale or exhale, device use compliance, etc.) and/or transmit such information to medical professionals. In some embodiments, the variable sense valve or e-monitoring chip can monitor the chemical composition of the exhaled air for purposes such as, for example, compliance to medication, breath analysis, and bacterial analysis (e.g., to check for pneumonia or dental caries risk). Various variable sense valve or e-monitoring chip or pressure monitors are commercially available.

In some embodiments, the pump 540 is a billow-type pump, an accordion-type pump, or a manual pneumatic pump. In some embodiments, the pump 540 is a billow-type pump. In some embodiments, the pump 540 is an accordion-type pump. In some embodiments, the pump 540 is a manual pneumatic pump. In some embodiments, the pump 540 is an electrical air pump. In some embodiments, the pump 540 is manual pump such as a bicycle type pump. In some embodiments, the pump 540 is capable of being actuated by hand, foot, or thigh. In some embodiments, the pump 540 further comprises one or more straps (not shown). In some embodiments, the straps are self-retaining straps. The straps can be configured to secure the pump 540 to the body of the user. In some embodiments, the pump can be powered by a single battery or a plurality of batteries, such as a portable battery or portable batteries. In some embodiments, the battery or batteries can be non-rechargeable or rechargeable.

Figure 2:
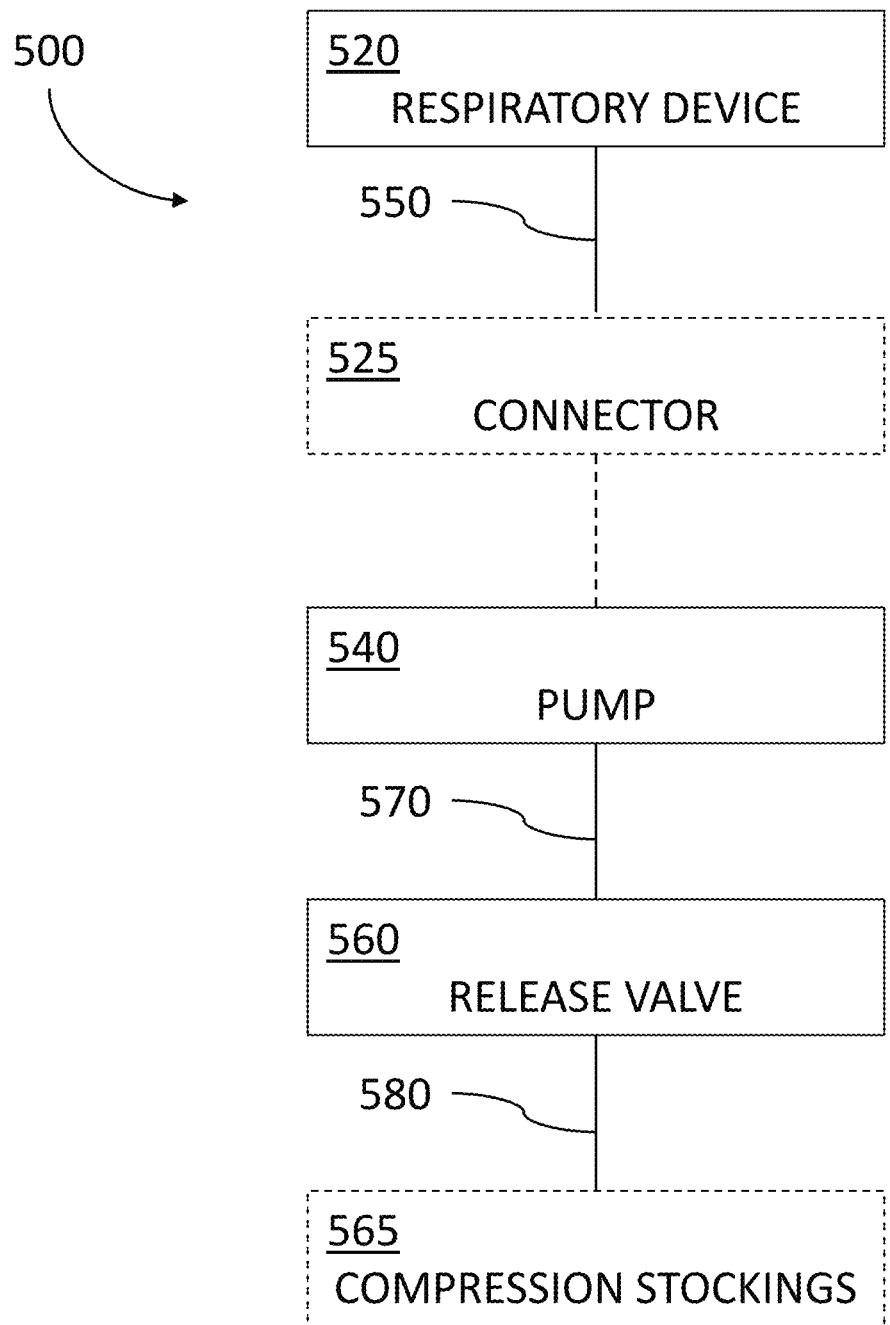
FIG. 2 shows a schematic diagram of an example multipurpose device according to the disclosure.

In some embodiments, and as shown in FIG. 2, the first tubing 550 connecting the pump 540 to the respiratory device 520 comprises a connector 525 that is capable of disconnecting the first tubing 550 from the pump 540. The connector 525 can be permanently located on the first tubing 550 such that when the first tubing 550 is disconnected from the pump 540, the first tubing 550 retains the connector 525. Alternately, the connector 525 can be permanently located on the pump 540 such that when the first tubing 550 is disconnected from the pump 540, the pump 540 retains the connector 525. The connector 525 allows the breathing function of the device 500 to be separated from the compression function of the device 500. The connector 525 allows interchangeability of various breathing components with various compression components. In some embodiments, a kit can comprise the breathing function of the device 500, or the compression function of the device 500, or both the breathing function of the device 500 and the compression function of the device 500. In these kits, the connector 525 can either be permanently located on the first tubing 550 such that when the first tubing 550 is disconnected from the pump 540, the first tubing 550 retains the connector 525, or the connector 525 can be permanently located on the pump 540 such that when the first tubing 550 is disconnected from the pump 540, the pump 540 retains the connector 525.

In some embodiments, the release valve 560 comprises a variable sense valve or e-monitoring chip 620. Such a valve or chip 620 can be configured to record compression information (e.g., compression levels, compression times, device use compliance, etc.) and/or transmit such information to medical professionals. Variable sense valves and e-monitoring chips 620 can be any of the commercially available variable sense valves and e-monitoring chips.

In some embodiments, the one or more third tubing(s) 580 comprise graduated color or markings 630 and an indicator ball or plunger 640. Upon activating the pump 540, the indicator ball or plunger 640 can travel within the third tubing(s) 580 and the length traveled can be determined by examining the graduated color or markings 630 on the third tubing(s) 580. The distance the indicator ball or plunger 640 moves can be an indication of the intensity of the compression of the compression stockings 565. In some embodiments, the one or more third tubing(s) 580 comprises a connector (not shown) at the terminal end(s). The connector connects the third tubing 580 to a compression stocking 565. In some embodiments, one or more compression stockings 565 are connected to the one or more third tubing(s) 580 by the connector at the terminal end(s).

The first tubing 550, second tubing 570, and third tubing(s) 580 can be made of any material that is impermeable to air, such as, for example, various plastics. First tubing 550, second tubing 570, and third tubing(s) 580 can be made of an expandable material (e.g., natural or synthetic rubber, polymer, foam, nylon, latex, silicone, etc.). The first tubing 550, second tubing 570, and third tubing(s) 580 can be any of the commercially available tubings. In addition, the first tubing 550, second tubing 570, and third tubing(s) 580 can be of variable length and can be made of expandable material.

The present disclosure also provides methods of using any of the devices 500 described herein comprising: inserting the air import 510 of the device 500 into the mouth or nose of a user; and inhaling or exhaling by the user via the respiratory device 520. In embodiments whereby the device 500 further comprises one or more compression stockings 565 connected to the one or more third tubing(s) 580 by the connector at the terminal end(s), the method further comprises activating the pump 540 to load the one or more compression stockings 565 with air. In some embodiments, compression stockings 565 are filled up to a pressure of about 20 mmHg. In some embodiments, compression stockings 565 are filled up to a pressure of about 30 mmHg. In some embodiments, compression stockings 565 are filled up to a pressure of about 40 mmHg. In some embodiments, compression stockings 565 are filled up to a pressure of about 50 mmHg. In some embodiments, compression stockings 565 are filled up to a pressure of about 60 mmHg. In some embodiments, compression stockings 565 are filled up to a pressure of about 70 mmHg.

In some embodiments, atalectasis is being treated or prevented in the user. In some embodiments, the user has asthma or chronic obstructive pulmonary disease and is undergoing breathing exercises. In some embodiments, the user is undergoing relaxation breathing therapy or diversion therapy. In some embodiments, the device is used to prevent or slow the progression of pneumonia. In some embodiments, the user is being treated to prevent deep vein thrombosis. In some embodiments, the device is used to prevent or slow the progression of lymphedema.

In some embodiments, the device 500 can be used by an athlete or entertainment performer in order to increase respiratory function and/or reduce edema and/or prevent DVT formation.

The present disclosure also provides methods of treating or preventing atelectasis comprising using any of the multipurpose devices described herein. The present disclosure also provides methods of treating asthma or preventing an asthma attack comprising using any of the multipurpose devices described herein. The present disclosure also provides methods of treating or preventing chronic obstructive pulmonary disease comprising using any of the multipurpose devices described herein. The present disclosure also provides methods of inducing relaxation or diversion comprising using any of the multipurpose devices described herein. The present disclosure also provides methods of treating or preventing deep vein thrombosis comprising using any of the multipurpose devices described herein. The present disclosure also provides methods of preventing or slowing the progression of pneumonia comprising using any of the multipurpose devices described herein. The present disclosure also provides methods of preventing or slowing the progression of lymphedema comprising using any of the multipurpose devices described herein. The present disclosure also provides methods of recuperating after an athletic training session comprising using any of the multipurpose devices described herein.

The compression stockings 565 described herein can be any of the commercially available compression stockings. In some embodiments, the compression stocking 565 is a pneumatic compression stocking. In some embodiments, the compression stocking 565 is for compressing a limb. The limb can be any limb of a mammal, particularly a human, such as an arm or a leg. In some embodiments, the limb is a leg. In some embodiments, the limb is the lower portion of a leg (i.e., blow the knee). In some embodiments, the compression stocking 565 can be in the form of a sock, stocking, sleeve, shirt, band, legging, or pants.

The present disclosure is not limited to the embodiments described and exemplified above, but is capable of variation and modification within the scope of the appended claims.

What is claimed is:

1. A multipurpose device comprising:
   a respiratory device configured to provide respiratory treatment to a user, the respiratory device comprising at least one of a spirometer or a flutter valve; and
   a pump configured to couple to the at least one of the spirometer or the flutter valve via first tubing such that air from the at least one of the spirometer or the flutter valve flows into the pump;
   a release valve connected to the pump via second tubing; and
   at least one third tubing connected to the release valve and configured to couple to at least one compression device configured to provide compression therapy to the user;
   wherein the pump is configured to provide air to the at least one therapeutic compression device through the at least one third tubing.

2. The device according to claim 1, wherein the respiratory device comprises the spirometer, and wherein the spirometer is an incentive spirometer, a peak flow spirometer, a windmill-type spirometer, a tilt-compensated spirometer, or fully electronic spirometer.

3. The device according to claim 2, wherein the spirometer is an incentive spirometer.

4. The device according to claim 1, wherein the respiratory device comprises a mouthpiece or a nasal breathing piece.

5. The device according to claim 4, wherein the mouthpiece is a disposable mouthpiece, permanent mouthpiece, or a one-way valve mouthpiece.

6. The device according to claim 4, wherein the respiratory device comprises a receptor for an insert adjacent to the mouthpiece or the nasal breathing piece.

7. The device according to claim 1, wherein the respiratory device comprises graduated color or markings and an indicator ball or plunger.

8. The device according to claim 1, wherein at least one of the first tubing, the second tubing, or the at least one third tubing has variable length.

9. The device according to claim 1, wherein the first tubing is expandable.

10. The device according to claim 1, wherein the pump is a billow-type pump, an accordion-type pump, or a manual pneumatic pump.

11. The device of claim 10, wherein the pump is capable of being actuated by hand, foot, or thigh.

12. The device according to claim 1, wherein the at least one third tubing comprises graduated color or markings and an indicator ball or plunger.

13. The device according to claim 1, wherein the at least one compression device comprises one or more compression stockings to allow gas to move from the pump to the one or more compression stockings.

14. The device according to claim 1, wherein the first tubing connecting the pump to the respiratory device comprises a connector that is capable of disconnecting the first tubing from the pump.

15. A method of using the multipurpose device according to claim 1, comprising:
   inserting a mouthpiece or a nasal breathing piece of the respiratory device into the mouth or nose of the user; and
   inhaling and/or exhaling by the user via the respiratory device.

16. The method of claim 15 further comprising activating the pump to load one or more compression stockings of the at least one compression device coupled to the at least one third tubing with air.

17. The method of claim 16, wherein the user is being treated to prevent deep vein thrombosis.

* * * * *